(12) United States Patent
Mallard et al.

(10) Patent No.: US 11,154,565 B2
(45) Date of Patent: *Oct. 26, 2021

(54) PROCESS FOR PREPARING A STABLE EMULSION COMPRISING ONE OR MORE AVERMECTINS

(71) Applicant: GALDERMA HOLDING SA, La Tour-de-Peilz (CH)

(72) Inventors: Claire Mallard, Mougins (FR); Richard Dugat, Rumilly (FR); Elodie Roger, Cagnes-sur-mer (FR); Ricardo Diaz, Sevrier (FR)

(73) Assignee: Galderma Holding SA, La Tour-de-Peilz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/766,746

(22) PCT Filed: Oct. 13, 2016

(86) PCT No.: PCT/EP2016/074624
§ 371 (c)(1),
(2) Date: Apr. 6, 2018

(87) PCT Pub. No.: WO2017/064205
PCT Pub. Date: Apr. 20, 2017

(65) Prior Publication Data
US 2018/0289732 A1 Oct. 11, 2018

(30) Foreign Application Priority Data
Oct. 13, 2015 (EP) .................................... 15306622

(51) Int. Cl.
| | |
|---|---|
| *A61K 9/107* | (2006.01) |
| *A61K 31/7048* | (2006.01) |
| *A01N 43/90* | (2006.01) |
| *A61K 47/10* | (2017.01) |
| *A61P 17/10* | (2006.01) |
| *A61P 17/08* | (2006.01) |
| *A61P 17/04* | (2006.01) |
| *A01N 25/04* | (2006.01) |

(52) U.S. Cl.
CPC .......... *A61K 31/7048* (2013.01); *A01N 25/04* (2013.01); *A01N 43/90* (2013.01); *A61K 9/107* (2013.01); *A61K 47/10* (2013.01); *A61P 17/04* (2018.01); *A61P 17/08* (2018.01); *A61P 17/10* (2018.01)

(58) Field of Classification Search
CPC .... A61K 31/7048; A61K 47/10; A61K 9/107; A01N 25/04; A01N 43/90; A61P 17/08; A61P 17/10; A61P 17/04
USPC ......................................................... 514/30
See application file for complete search history.

(56) References Cited

U.S. PATENT DOCUMENTS

| | | |
|---|---|---|
| 2009/0035338 A1 | 2/2009 | Segura-Orsini et al. |
| 2009/0136574 A1 | 5/2009 | Diaz-Astruc et al. |
| 2009/0227668 A1 | 9/2009 | Manetta et al. |

FOREIGN PATENT DOCUMENTS

WO 2007/119028 A2 10/2007

OTHER PUBLICATIONS

Tippetts (Thesis: "Effect of Processing and Formulation Conditions on Physicochemical Characteristics of Food Emulsions" by Megan Tippetts, Master of Science, Utah State University; 2008, i-xii, 1-122).*
International Search Report dated Feb. 8, 2017 corresponding to International Patent Application No. PCT/EP2016/074624, 3 pages.
Written Opinion of the International Searching Authority dated Feb. 8, 2017 corresponding to International Patent Application No. PCT/EP2016/074624, 5 pages.

* cited by examiner

*Primary Examiner* — Shaojia A Jiang
*Assistant Examiner* — Michael C Henry
(74) *Attorney, Agent, or Firm* — Foley & Lardner LLP; Sunit Talapatra

(57) ABSTRACT

A process is described for preparing a stable emulsion that includes at least one avermectin. Also described, is the emulsion thus obtained, especially for use in the treatment of dermatological disorders such as rosacea.

8 Claims, 4 Drawing Sheets

PROCESS FOR PREPARING A STABLE EMULSION COMPRISING ONE OR MORE AVERMECTINS

CROSS-REFERENCE TO PRIOR APPLICATIONS

Figure 1A:
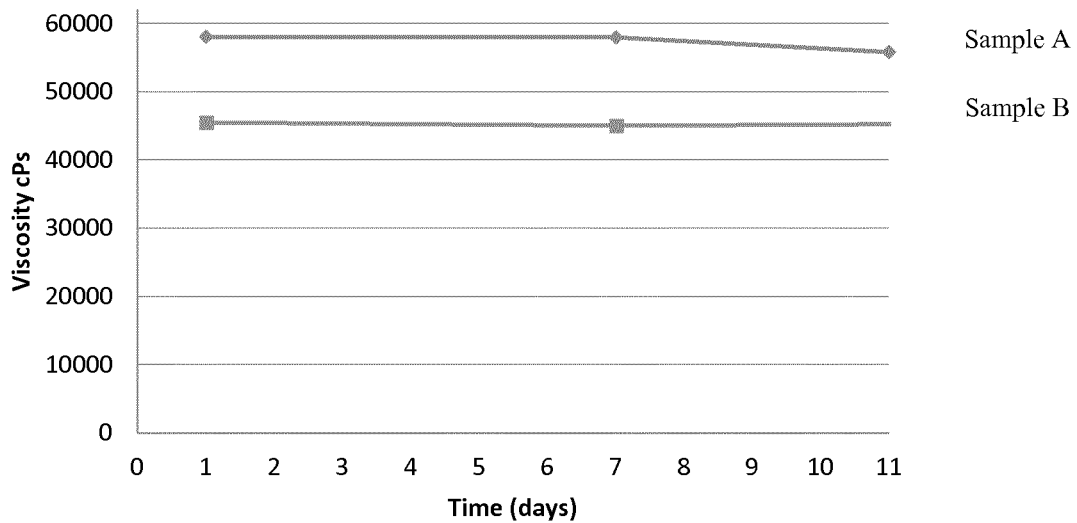

This application is a National Stage of PCT/EP2016/074624 filed Oct. 13, 2016, and designating the United States (published on Apr. 20, 2017, as WO 2017/064205 A1), which claims priority under 35 U.S.C. § 119 to European Patent Application No. 15306622.0, Oct. 13, 2015, each hereby expressly incorporated by reference in its entirety and each assigned to the assignee hereof.

FIELD OF THE INVENTION

The present invention pertains to a process for preparing a stable emulsion comprising or more avermectins. It is also directed to the emulsion thus obtained, especially for use in the treatment of dermatological disorders such as rosacea.

BACKGROUND OF THE INVENTION

Avermectins are macrocyclic lactones having potent anti-helmintic and insecticidal properties, which are obtained by fermentation of *Streptomyces avermitilis*, a soil actinomycete. Among avermectins, mention can be made of ivermectin, selamectin, doramectin and abamectin. Ivermectin is itself a mixture of two compounds, namely 5-O-demethyl-22,23-dihydroavermectin A1a and 5-O-demethyl-22,23-dihydroavermectin A1b. They are also known under the trademarks of 22,23-dihydroavermectin B1a and 22,23-dihydroavermectin B1b. Ivermectin comprises at least 80% of 22,23-dihydroavermectin B1a and less than 20% of 22,23-dihydroavermectin B1b.

In the middle of the 1980s, ivermectin was presented as a broad-spectrum anti-parasitic medicament for veterinary use, as it is effective against the majority of common intestinal worms (except for the Teniae), the majority of the acarids and a few lice. In humans, ivermectin is more particularly used as an anthelmintic, in the treatment of onchocerciasis due to *Onchocerca volvulus*, of gastrointestinal strongyloidiasis (anguillulosis) and of human scabies. More recently, it has been suggested to use ivermectin for the treatment of dermatological disorders such as rosacea (WO 2004/093886). A cream comprising 1% ivermectin has been approved by the FDA for the topical treatment of inflammatory lesions of rosacea (Soolantra®).

In the case where ivermectin is formulated for topical application, it is advantageous to incorporate it in an emulsion which may be easily spread onto skin. However, ivermectin is unstable in the presence of water, which can result in chemical instability of the active principle and/or in crystallization of the initially dissolved active principle. This may in turn detrimentally affect the overall stability of the compositions containing ivermectin, including their viscosity and their appearance. In order to reduce or prevent this phenomenon, it has already been suggested to dissolve ivermectin in propylene glycol before mixing it with an aqueous phase and an oil phase forming an oil-in-water emulsion stabilized with a polymeric emulsifier (FR 2 867 684). Another solution was provided in U.S. Pat. No. 8,287,891, which consists in formulating ivermectin in an inverse emulsion wherein a significant portion of the aqueous phase is replaced with glycols, so as to obtain a glycol-in-oil emulsion. Another stable emulsion of ivermectin has been proposed in U.S. Pat. No. 8,080,530. This emulsion is prepared by first emulsifying an aqueous phase with an oil phase at high temperature (70° C.) under stirring, then cooling down the resulting emulsion to 40° C. before introducing therein an active phase comprising ivermectin dissolved in propylene glycol and then allowing the emulsion to cool to 30° C.

Although these prior attempts have allowed formulating ivermectin in emulsions which remain stable despite temperature and/or pH variations, it has been observed that the viscosity of some emulsions containing ivermectin, such as those described in U.S. Pat. No. 8,080,530, tended to increase by 30 to 60% and until 150% in the worst case, during the week following their manufacture. Without being bound by this theory, it is assumed that this increase in viscosity is due to the swelling in water of lamellar structure formed by the non-ionic surfactants and fatty alcohols initially present in the oily phase, once both phases have been brought together and cooled. In order to ensure a sustainable product quality, it is thus necessary to retain the composition during this maturing time, until the viscosity has become constant, before release the bulk product. Of course, this holding time negatively impacts the economics of the manufacturing process.

In view of the foregoing, there remains the need for a stable emulsion comprising at least one avermectin, whose viscosity does not substantially evolve during the weeks following its manufacture.

SUMMARY OF THE INVENTION

The Applicant has now surprisingly found that a stable emulsion comprising at least one avermectin may be obtained by controlling the cooling rate of the emulsion after introducing therein the active phase comprising the avermectin.

Thus, this invention is directed to a process for preparing a composition in the form of an emulsion comprising at least one avermectin, comprising the following successive steps:

(a) preparing an oily phase and an aqueous phase, (b) emulsifying said oily and aqueous phases at a temperature of from 60 to 75° C., (c) cooling the resulting emulsion to a temperature of from 48 to 55° C., (d) adding to said emulsion an active phase containing at least one avermectin dissolved in a medium comprising at least one glycol, and (e) cooling said emulsion to a target temperature of from 30 to 40° C., characterized in that, in step (e), said emulsion is subjected to a controlled cooling to said target temperature.

According to a first embodiment, said emulsion is cooled at a cooling rate from 0.5° C. to 1.5° C./5 min, preferably from 0.8 to 1.5° C./5 min, more preferably of 1° C./5 min.

According to a second embodiment, the controlled cooling comprises cooling down said emulsion to a temperature plateau comprised between 42 and 47° C., then maintaining a temperature plateau, preferably for 10 to 20 minutes, and further cooling said emulsion to said target temperature.

It is also directed to a composition in the form of an emulsion comprising at least one avermectin, characterized in that the Brookfield viscosity of said composition, when stored at room temperature for 7 days immediately after manufacturing, does not vary by more than 10% and preferably by not more than 5%, compared to the viscosity measured immediately after manufacturing.

This invention is also directed to the above composition for use in the treatment of a dermatological disorder such as rosacea, atopic dermatitis, hand eczema, common acne, seborrheic dermatitis, perioral dermatitis, acneiform rashes, transient acantholytic dermatosis and acne necrotica miliaris, preferably rosacea.

This invention further pertains to a method for improving the stability of an emulsion comprising at least one avermectin, which is prepared according to a process comprising the following successive steps:

(a) preparing an oily phase and an aqueous phase, (b) emulsifying said oily and aqueous phases at a temperature of from 60 to 75° C., (c) cooling the resulting emulsion at a temperature of from 48 to 55° C., (d) adding to said emulsion an active phase containing at least one avermectin dissolved in a medium comprising at least one glycol, and (e) cooling said emulsion to a target temperature of from 30 to 40° C., characterized in that said method comprises subjecting said emulsion, in step (e), to a controlled cooling to said target temperature.

DETAILED DESCRIPTION

The manufacturing process of this invention comprises a first step of preparing an oily phase and an aqueous phase. This first step is preferably done at a temperature of from 60 to 75° C.

The aqueous phase may comprise from 30 to 95%, and preferably from 60 to 80% by weight of water, relative to the total weight of the composition. In addition, it may include at least one of: a gelling agent, such as carboxyvinyl polymers (Carbomers), cellulose derivatives, polysaccharide gums, homo- and copolymers of acrylamide, of alkyl acrylate, of acrylic acid, and/or of 2-acrylamido-2-methylpropane sulfonic acid (AMPS), clays and native or modified starches; a polyol such as glycerin; a chelating agent; a pH adjusting agent; and mixtures thereof. Preferably, at least one gelling agent is included within the aqueous phase.

The oily phase may comprise at least one oil, which may be selected from vegetable, mineral, animal and/or synthetic oils, such as alkyl esters, silicone oils, paraffin oils and mixtures thereof. In addition, the oily phase may include at least one thickening agent which may be selected from linear fatty alcohols, for instance stearyl and/or cetyl alcohol, linear fatty acids, vegetable waxes, silicone gums and mixtures thereof. Preferably, at least one linear fatty alcohol, comprising from 12 to 20 carbon atoms, is included within the oily phase. The ingredients of the oily phase may be selected in a varied manner by those skilled in the art in order to prepare a composition having the desired properties, for example of consistency or of texture. The oily phase may represent from 3 to 50%, preferably from 10 to 20% by weight, relative to the total weight of the composition.

The aqueous and/or oily phase may further include at least one of: a preservative such as an alkyl parahydroxybenzoate (paraben), phenoxyethanol and mixtures thereof; an antioxidant; an emulsifier such as a sorbitan ester, a polyoxyethylene ether of fatty alcohol, a polyoxyethylene fatty acid ester, a glyceryl ester; and mixtures thereof. Preferably, at least one non-ionic surfactant is included within the oily phase.

In the second step of the process according to this invention, said oily and aqueous phases are emulsified at a temperature of from 60 to 75° C., by introducing the oily phase into the aqueous phase under stirring. It is preferred that both the aqueous and oily phases are heated to said temperature before mixing. Such pre-heating steps may be initiated at any stage during the preparation of the aqueous and oily phases. It will be readily apparent for the skilled artisan which constituents should be added prior to heating and which should be added only after. This step is preferably performed at a temperature of from 60 to 70° C., preferably at a temperature of 65° C.±2° C. The resulting oil-in-water emulsion is then cooled down to a temperature of from 48 to 55° C., preferably at 50° C.±2° C.

Then, an active phase containing at least one avermectin dissolved in a medium comprising at least one glycol is introduced into said emulsion. The active phase is preferably heated to the same temperature as the emulsion before introducing the former into the latter. This pre-heating step may be initiated at any stage during the preparation of the active phase and preferably before adding the avermectin therein.

The active phase can usually contain from 0.01 to 3%, preferably 0.1 to 2.5%, more preferably from 0.1 to 2%, still more preferably from 0.5 to 1%.

According to a preferred embodiment of this invention, the active phase preferably contains 1% by weight of avermectin, relative to the total weight of the composition.

Examples of avermectins useful according the present invention, include: invermectin, ivermectin, avermectin, abamectin, doramectin, eprinomectin, selamectin and optical isomers thereof. According to a preferred embodiment of this invention, said avermectin is selected from ivermectin and optical isomers thereof. The glycol may represent from 0.5 to 15% by weight, and preferably from 1 to 8% by weight, relative to the total weight of the composition. Examples of glycols are (C1-C6) alkylene glycols and poly(C1-C6) alkylene glycols, such as ethylene glycol, propylene glycol, polyethylene glycol, polypropylene glycol, butylene glycol, pentylene glycol and hexylene glycol and their mixtures. A preferred glycol is propylene glycol. The glycol may be mixed with one or more monohydric alcohols selected from C1-C6 monohydric alcohols, such as ethanol, isopropanol and butanol, C12 to C32 linear unsaturated or branched saturated monohydric alcohols, such as oleyl alcohol or Guerbet alcohols, polyhydric alcohols other than glycols, such as glycerol; and mixtures thereof. According to an embodiment of this invention, the active phase comprises a mixture of propylene glycol and oleyl alcohol in a weight ratio of from 1:4 to 4:1 and preferably of 1:1. According to an embodiment, the active phase represents from 1 to 18% of the total weight of the composition.

An emulsion is thus obtained, which is then cooled down, in the next step of the process according to this invention, to a target temperature of from 30 to 40° C., preferably at 35° C.±2° C., by subjecting said emulsion to a controlled cooling to said target temperature.

According to a first embodiment, said controlled cooling comprises, or preferably consists in, cooling said emulsion at a cooling rate of from 0.5 to 1.5° C./5 min, preferably from 0.8 to 1.5° C./5 min, and more preferably of 1° C./5 min, usually with a temperature regulation system. Such cooling step is controlled by a linear and regular decrease of temperature depending on time. For instance, said emulsion is subjected to a cooling rate of from 0.5 to 1.5° C. every 5 min, preferably from 0.8 to 1.5° C. every 5 min and more preferably of 1° C. every 5 min. This specific cooling step will be named "cooling ramp" in the further description and examples.

According to a second embodiment, said controlled cooling comprises, and preferably consists in, cooling said emulsion to a temperature comprised between 42 and 47° C., preferably at 45° C., then maintaining a temperature plateau, preferably for 10 to 20 minutes, and further cooling said emulsion to said target temperature. Such cooling step is controlled by maintaining the temperature between 42 and 47° C., also called a temperature plateau, preferably during 10 to 20 minutes. For instance, said emulsion is first subject to a cooling at a temperature comprised between 42 and 47° C., and then maintaining at this temperature plateau preferably during 10 to 20 minutes. This specific cooling step will be named "cooling plateau" in the further description and examples.

These embodiments of the invention allow improving the stability of the composition and especially avoiding large viscosity changes immediately after manufacture. Without being bound by this theory, it is assumed that this increase in viscosity is due to the swelling in water of lamellar structure formed by the non-ionic surfactants and fatty alcohols initially present in the oily phase, once both phases have been brought together and cooled.

The cooling step is preferably performed while stirring the emulsion.

The resulting emulsion may then be further cooled down to room temperature, i.e. from 20 to 25° C., optionally after adding a neutralizing agent, such as a base, to the emulsion (which may be required in the case where the gelling agent bears acidic groups, for instance when a Carbomer is used).

The process as described above enhances the physical stability of a composition comprising at least one avermectin and more specifically maintains a substantially constant viscosity after manufacturing.

Hence, the viscosity of the composition that may be obtained according to the above process, when stored at room temperature for 7 days compared to the viscosity measured immediately after manufacturing, does not vary by more than 10%, preferably not by more than 5%. Such viscosity may be measured at room temperature (20-25° C.) by a Brookfield viscosimeter RV DVII equipped with a #34 spindle rotating at 6 rpm.

Moreover, in some embodiments of this invention, the composition can further be chemically stable, such that no recrystallization of avermectin may be observed.

This composition may be used in the treatment of a dermatological disorder such as rosacea, atopic dermatitis, hand eczema, common acne, seborrheic dermatitis, perioral dermatitis, acneiform rashes, transient acantholytic dermatosis and acne necrotica miliaris, preferably rosacea.

FIGURES

FIG. 1A: Viscosity evolution over 11 days of ivermectin 1% cream at 1 kg obtained by Process A (Samples A and B).

Figure 1B:
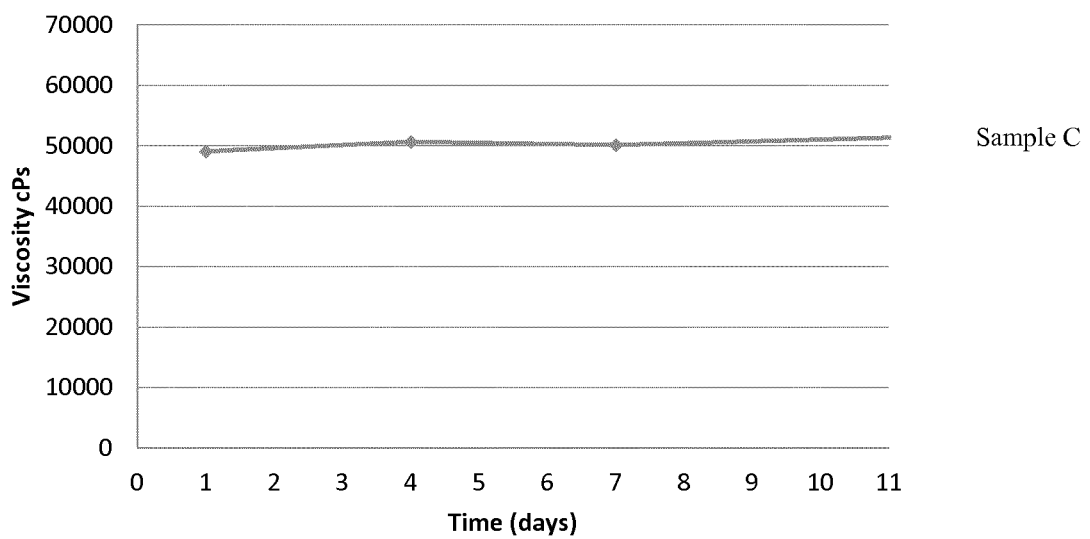

FIG. 1B: Viscosity evolution over 11 days of ivermectin 1% cream at 50 kg obtained by Process A (Sample C).

Figure 2:
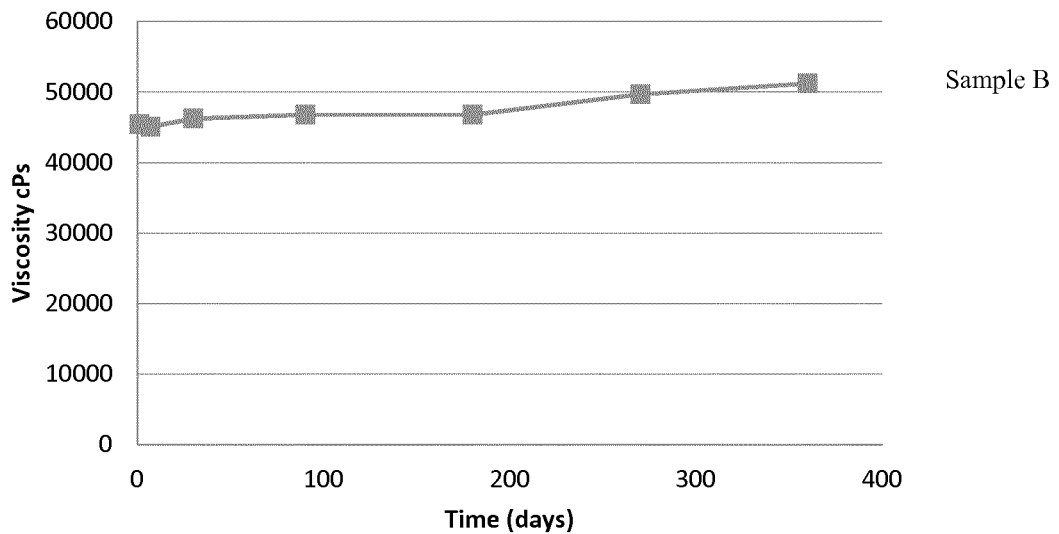

FIG. 2: Viscosity evolution over 12 months at room temperature of ivermectin 1% cream at 1 kg obtained by Process A (Sample B).

Figure 3:
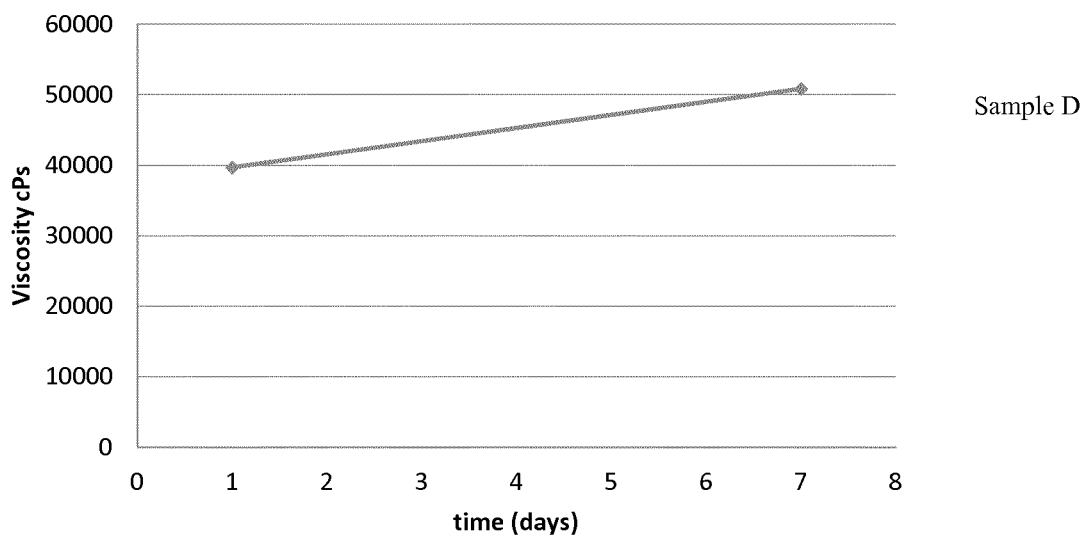

FIG. 3: Viscosity evolution over 7 days of ivermectin 1% cream at 1 kg obtained by Process B (Sample D).

Figure 4A:
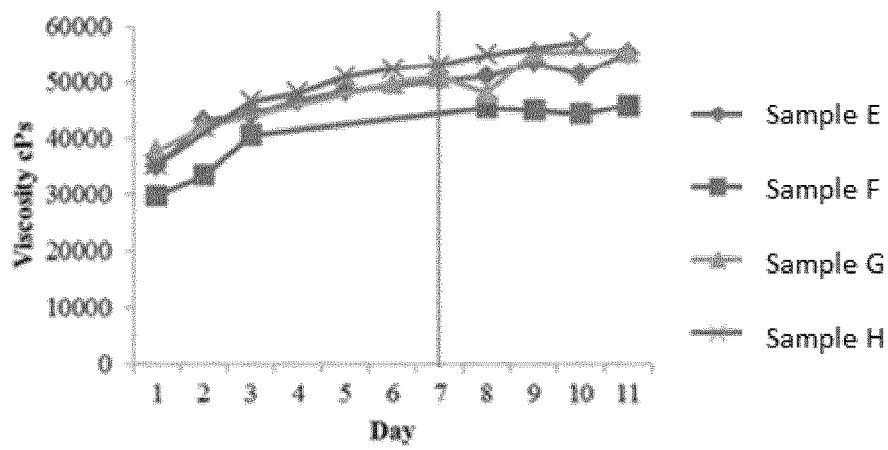

FIG. 4A: Viscosity evolution over 11 days of ivermectin 1% cream at 2000 kg obtained by Process B (Samples E, F, G, and H).

Figure 4B:
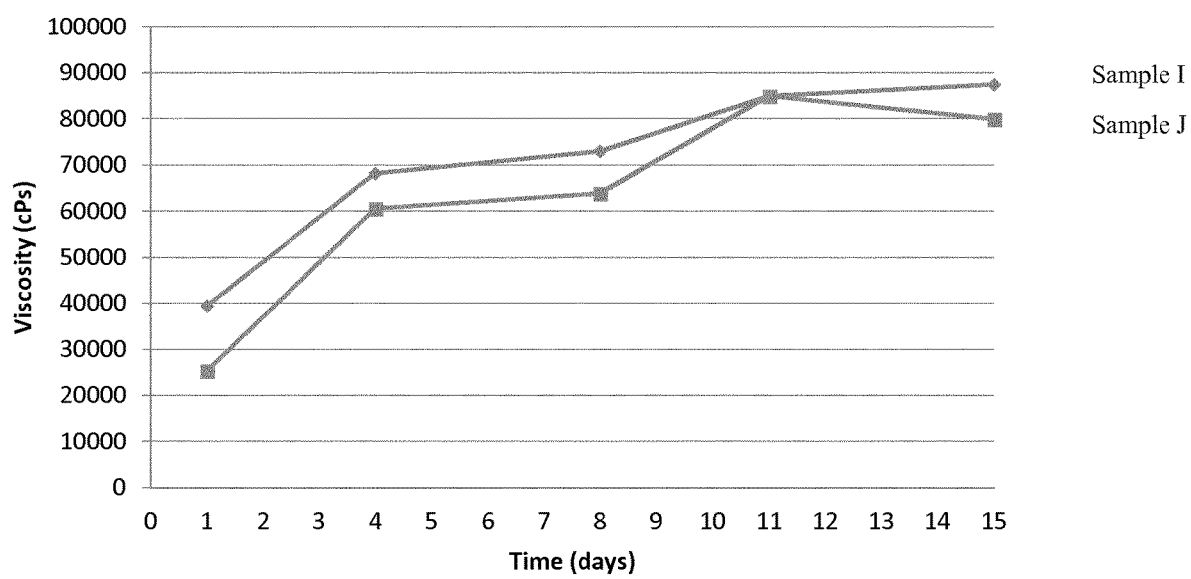

FIG. 4B: Viscosity evolution over 15 days of ivermectin 1% cream at 1000 kg obtained by Process B (Samples I and J).

Figure 5:
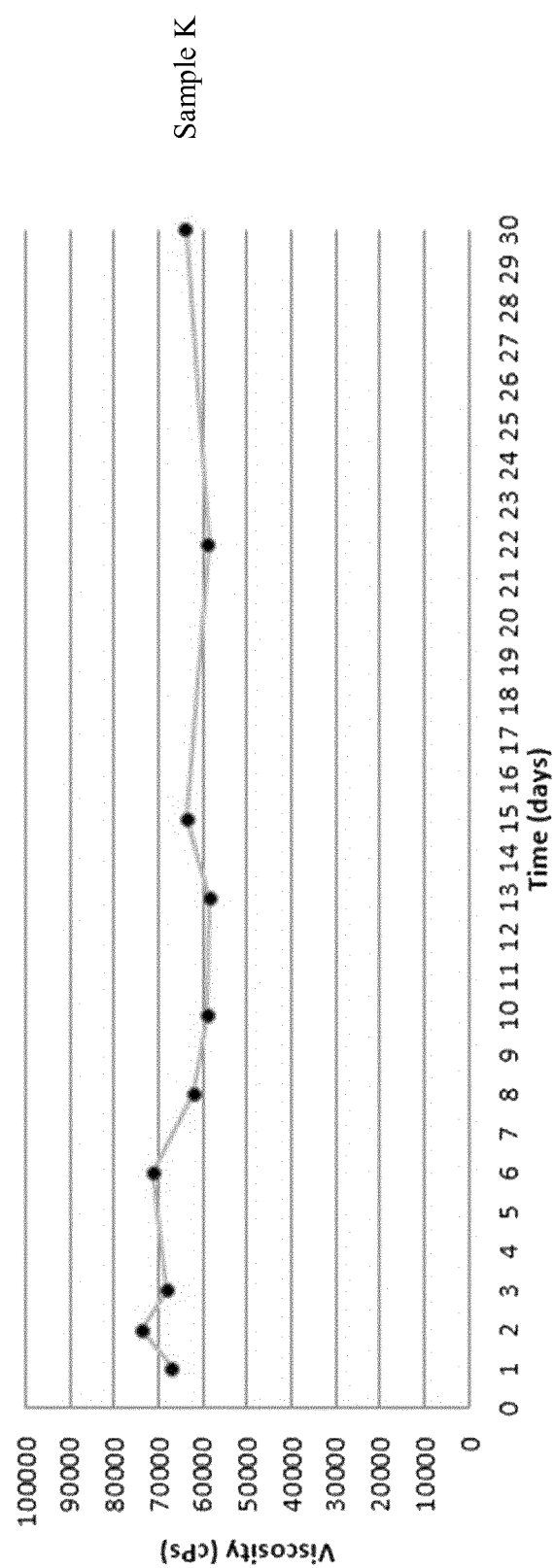

FIG. 5: Viscosity evolution over 30 days of ivermectin 1% cream at 1000 kg obtained by Process A (Sample K).

EXAMPLES

This invention will be better understood in light of the following examples which are given for illustrative purposes only and do not intend to limit the scope of the invention, which is defined by the attached claims. In the following examples, the process according to the present invention comprising a controlled cooling step is named Process A. The process according to example 2, i.e. with no controlled cooling step, is named Process B.

Example 1: Preparation of a Cream with 1% Ivermectin Obtained by Process A

The composition described in table 1 below was prepared by Process A.

TABLE 1

| PHASE | INCI NAME | % W/W |
|---|---|---|
| OILY PHASE | ISOPROPYL PALMITATE | 4.0 |
| | CETYL ALCOHOL | 3.5 |
| | STEARYL ALCOHOL | 2.5 |
| | CETEARETH-20 | 3.0 |
| | SORBITAN MONOSTEARATE | 2.0 |
| | DIMETHICONE | 0.5 |
| | PROPYL PARAHYDROXYBENZOATE | 0.1 |
| AQUEOUS PHASE | CARBOMER COPOLYMER TYPE B | 0.2 |
| | GLYCERIN | 4.0 |
| | METHYL PARAHYDROXYBENZOATE | 0.2 |
| | DISODIUM EDTA | 0.05 |
| | CITRIC ACID | 0.05 |
| | PHENOXYETHANOL | 1.0 |
| | WATER | QSP 100 |
| ACTIVE PHASE | PROPYLENE GLYCOL | 2.0 |
| | OLEYL ALCOHOL | 2.0 |
| | IVERMECTIN | 1.0 |
| NEUTRALIZING AGENT | NAOH 1% SOLUTION | QS | a) Preparation of the Three Phases:

The water phase was made by dispersing the gelling agent in water in a first tank, under shear until a homogenous gel was obtained. After heating at a temperature comprised between 60° C. and 75° C., preferably 65° C.±2° C., glycerol and the remaining constituents of the aqueous phase were added.

The oily phase was made separately by mixing the ingredients in a second tank and heated at a temperature comprised between 60° C. and 75° C., preferably 65° C.±2° C. under stirring until the mixture is homogeneous.

The active phase was made by introducing solvents into a third tank, heated at 50° C. and homogenized. Ivermectin was weighted in a weighing boat and then added to this tank, which was then stirred until ivermectin was fully dissolved.

b) Emulsification Step:

When the oily and aqueous phases were at the same heating temperature, preferably around 65° C., the two phases were mixed under shear for 10 min. The emulsion thus formed was allowed to cool to 50° C., then the active phase was added thereto under shear.

The controlled cooling step was then performed from 50° C. to 35° C. with a temperature plateau at 45° C. during 15 minutes (the "cooling plateau" step) or with a cooling rate of 1° C./5 min with constant shear rate (the "cooling ramp" step).

A neutralizing agent was then added at 35° C. until the pH was comprised between 6.0 and 6.6 and the composition was further cooled to room temperature. A white to pale yellowish cream was thus obtained.

The above process was conducted at laboratory scale on a 1 kg batch of composition (Samples A and B), at pilot scale on a 50 kg batch of composition (Sample C), and at industrial scale on 1000 kg batch of composition (Sample K).

Example 2: Preparation of a Cream with 1% Ivermectin Obtained by Process B

The same composition as that described in Table 1 was prepared on laboratory scale (1 kg batch, Sample D), and on industrial scale (1000 kg, Samples I and J; and 2000 kg, Samples E, F, G, and H) according to a process similar to that carried out in Example 1, except that:
- the aqueous and oily phases were pre-heated at 72° C. and emulsification was performed at this temperature,
- the emulsion was cooled from 50° C. to 35° C. within 10 to 45 minutes, thus at a cooling rate of from 2 to 8° C./5 min, either by leaving it at room temperature (lab scale) or by cooling it with a water jacket without any temperature control.

The significant difference with the example 1 process being that the emulsion was not subject to a controlled cooling step with a mean cooling rate below 2° C./5 min.

Example 3: Comparative Stability Tests of Compositions Obtained by Process A or by Process B The viscosity change of the batches prepared according to Examples 1 (Process A) and 2 (Process B) was assessed using a Brookfield viscosimeter RV DVII equipped with a #34 spindle rotating at 6 rpm.

As shown on FIGS. 1A (process A comprising a "cooling plateau" step) and 1B (process A comprising a "cooling ramp" step), the viscosity of the cream prepared according to the process of the invention does not vary by more than 10%, and more precisely not by more than 5% both on lab scale and on pilot scale, during the first week after manufacture.

As shown on FIG. 2 (process A comprising a "cooling plateau" step), the viscosity of the lab sample prepared according to the process of the invention does not even vary during the first 200 days and then only slightly changes over the next 200 days are observed.

As shown on FIG. 5 (Process A comprising a "cooling ramp step"), the viscosity of the industrial sample prepared according to the process of this invention does not vary by more than 10%, during the first week after manufacture, and not more than 5% during the second and first weeks after manufacture.

Conversely, as shown on FIGS. 3, 4A and 4B, the viscosity of the batches prepared according to Process B, which does not include a controlled cooling step, varies by 30% (on lab scale), up to 50% (on industrial scale 2000 kg), and up to 150% (on industrial scale 1000 kg) during the first week following manufacture, respectively.

These examples demonstrate that the process according to this invention (Process A) allows manufacturing a cream having a stable viscosity over time, with no maturation during the time, contrary to the comparative process (Process B).

Therefore, the process of this invention allows a better control of viscosity after manufacturing, which guarantees the quality of the product and positively impacts the economics of the manufacturing process.

In addition, according to the manufacturing process of the present invention as described in example 1, the emulsification temperature may be decreased to 65° C. without impairing the viscosity stability, which also improves the economics of the process.

Moreover, it has been checked that ivermectin is also chemically stable when the composition obtained according to this invention is stored for 6 months at 40° C. and for 12 months at room temperature.

The invention claimed is:

1. A process of preparing a composition in the form of an emulsion comprising 0.01% to 3% by weight of at least one avermectin, relative to the total weight of the composition, the process comprising, successively:
   (a) emulsifying an oily phase and an aqueous phases at a temperature from 60° C. to 75° C.;
   (b) cooling the resulting emulsion to a temperature from 48° C. to 55° C.;
   (c) adding to the emulsion an active phase comprising the at least one avermectin dissolved in a medium comprising at least one glycol; and
   (d) cooling the emulsion to a single temperature selected from 42° C. to 47° C.;
   (e) maintaining the temperature in (d) for 10 to 20 minutes; and
   (f) cooling the emulsion further to a temperature from 30° C. to 40° C.

2. The process according to claim 1, wherein the at least one avermectin is selected from the group consisting of ivermectin and optical isomers thereof.

3. The process according to claim 1, wherein the at least one avermectin is present in an amount from 0.1% to 2% by weight, relative to the total weight of the composition.

4. The process according to claim 1, wherein the at least one avermectin is present in an amount from 0.5% to 1% by weight, relative to the total weight of the composition.

5. The process according to claim 1, wherein the emulsifying is performed at 65° C.±2° C.

6. The process of claim 1, wherein the emulsion has a Brookfield viscosity that, when measured after the emulsion has been stored at room temperature for 7 days immediately after manufacturing, does not vary by more than 10% compared to the Brookfield viscosity measured immediately after manufacturing.

7. The process of claim 6, wherein the Brookfield viscosity of the emulsion, when measured after the emulsion has been stored at room temperature for 7 days immediately after manufacturing, does not vary by more than 5% compared to the Brookfield viscosity measured immediately after manufacturing.

8. The process of claim 1, wherein the cooling of (b), (d), and/or (f) of the emulsion is uncontrolled.

* * * * *